United States Patent [19]

Kesling

[11] Patent Number: 5,727,941
[45] Date of Patent: Mar. 17, 1998

[54] ARCHWIRE BUCCAL TUBE

[75] Inventor: Peter C. Kesling, LaPorte, Ind.

[73] Assignee: TP Orthodontics, Inc., Westville, Ind.

[21] Appl. No.: 835,122

[22] Filed: Apr. 4, 1997

[51] Int. Cl.[6] ............................................. A61C 3/00
[52] U.S. Cl. ........................................................ 433/17
[58] Field of Search ............................... 433/8, 9, 16, 17

[56] References Cited

U.S. PATENT DOCUMENTS

| | | | |
|---|---|---|---|
| 986,076 | 3/1911 | Montag | 433/17 |
| 1,481,861 | 1/1924 | Eaton | 433/17 |
| 3,815,238 | 6/1974 | Wallshein | |
| 4,842,512 | 6/1989 | Kesling | 433/8 |
| 4,859,179 | 8/1989 | Kesling | 433/8 |
| 4,877,398 | 10/1989 | Kesling | 433/8 |
| 4,963,092 | 10/1990 | Snead | 433/17 |
| 5,057,012 | 10/1991 | Kesling | 433/17 |
| 5,082,442 | 1/1992 | Rosen | 433/17 |
| 5,151,028 | 9/1992 | Snead | 433/17 |
| 5,292,248 | 3/1994 | Schultz | 433/17 |
| 5,556,277 | 9/1996 | Yawata et al. | 433/17 |

Primary Examiner—Nicholas D. Lucchesi
Attorney, Agent, or Firm—Lloyd L. Zickert

[57] ABSTRACT

A buccal tube for an archwire wherein the tube includes a lumen having a control portion at the mesial end and a relieved portion toward and at the distal end which reduces the force required for mesial withdrawal of the archwire after the archwire has been bent, and may also permit distal crown tipping of the tooth on which the tube is mounted.

18 Claims, 2 Drawing Sheets

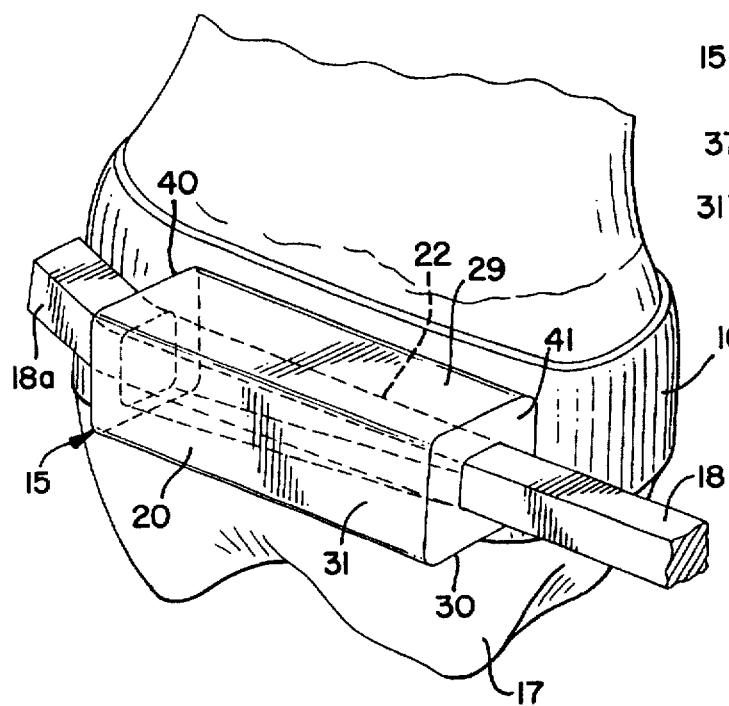
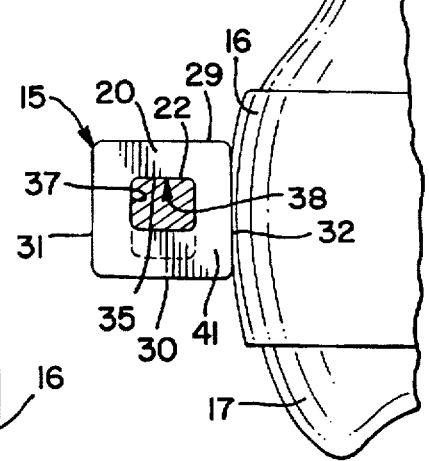
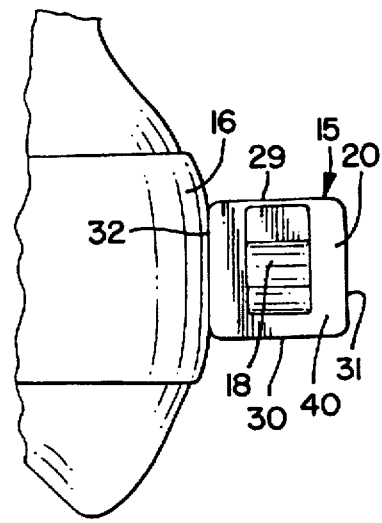
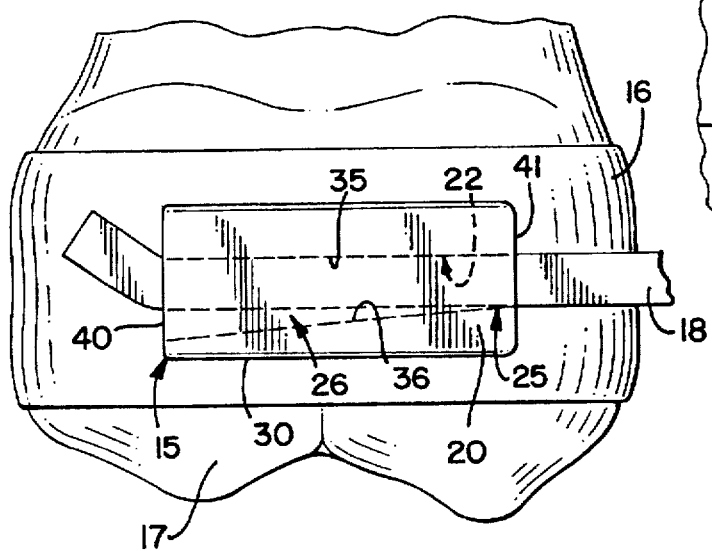

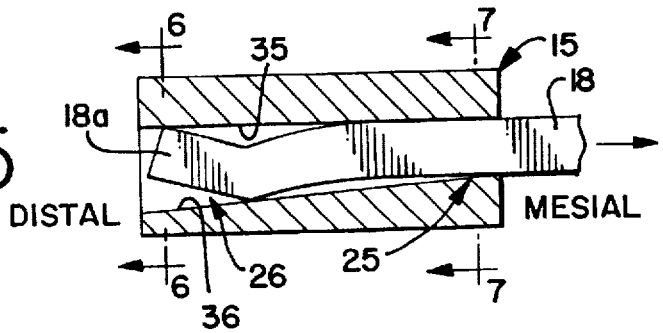
FIG. 5
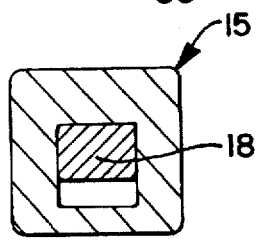
FIG. 6
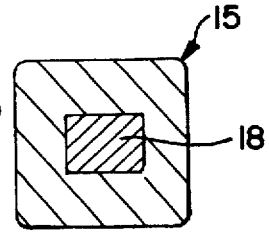
FIG. 7
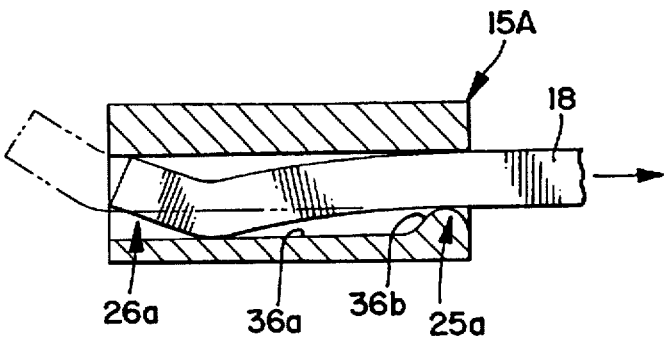
FIG. 8
FIG. 10
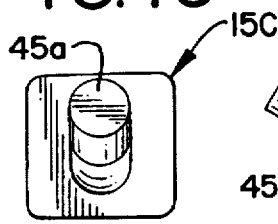
FIG. 9
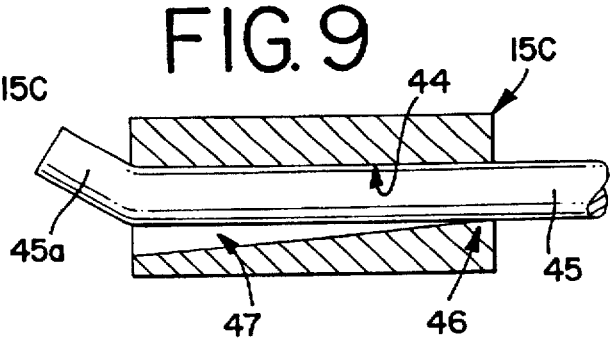
FIG. 11
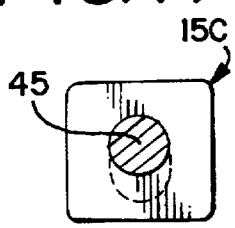
FIG. 12
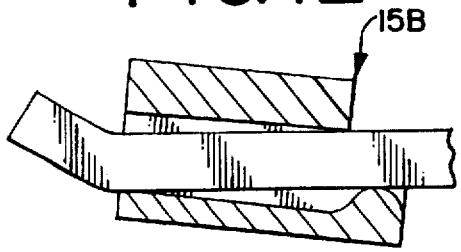
FIG. 13
PRIOR ART
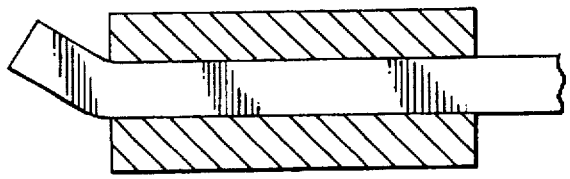

ARCHWIRE BUCCAL TUBE

DESCRIPTION

This invention relates in general to a molar tube, and more particularly to a molar tube for an archwire, and still more particularly to a molar tube that facilitates the withdrawal of an archwire after the archwire has been bent and may also permit distal crown tipping of the tooth on which the tube is mounted.

BACKGROUND OF THE INVENTION

Heretofore, there have been molar tubes for receiving archwires and having flared openings at the mesial end to facilitate the threading of the archwire into the tube, such as shown in U.S. Pat. No. 5,556,277. There have also been a number of molar tubes for lip bumpers and head gear having the inlet mesial end enlarged to facilitate the mounting of a lip bumper or head gear, such as shown in U.S. Pat. Nos. 3,815,238; 4,963,092; 5,057,012; 5,151,028; and 5,292,248. It is also known to provide a bracket that permits limited tipping relative to the archwire, as disclosed in U.S. Pat. Nos. 4,842,512; 4,859,179, and 4,877,398.

During orthodontic treatment and the use of fixed appliances on the teeth, including brackets for receiving an archwire, buccal tubes are employed to anchor the distal ends of the archwire. The buccal tubes are mounted on molar teeth which constitute the posterior teeth in the mouth. Following the placement of the distal ends of the archwire in buccal tubes, it is customary to trim the ends of the wire and then bend the ends that protrude from the distal ends of the tubes to prevent the archwire from moving mesially through the tubes which could result in spaces opening mesial to the anchor molars. It will be appreciated that the archwire is otherwise secured to brackets on the adjacent posterior and anterior teeth, and therefore it is important not to allow mesial movement of the archwire when the fixed appliances are in place. Additionally, the distal ends of the archwire are bent in a direction to prevent the ends from striking/irritating the patient's hard or soft tissues, the hard tissues being the enamel surfaces of the teeth, and the soft tissues being the gingiva or cheek.

During the course of treatment, it is often necessary to remove and replace the archwires with the bent ends. Such a procedure requires straightening the bent ends as much as possible and then pulling those bent ends mesially through the buccal tubes. Inasmuch as it is difficult, if not impossible, to completely straighten the ends of the wires, considerable forces are required to withdraw or pull the wires through the tubes. High amounts of force are first required to deflect the end of the wire so it can pass through the tube and second to overcome the friction created by drawing the deformed wire through the length of the tube. This is particularly the case where full size rectangular archwires are employed to fit rectangular tubes, wherein the tolerances are ±0.001 inch (0.025 mm). The application of the necessary forces to remove archwires having bent ends is unusually discomforting to the patient. It not only is discomforting by the force required but also because of the duration of that force as the archwire is pulled through the entire length of the tube. The well-being and comfort of a patient is particularly important as it can relate to the results achieved during orthodontic treatment.

SUMMARY OF THE INVENTION

The above-mentioned problem of patient discomfort is at least partially solved by the present invention wherein the buccal tube of the present invention reduces the force required to mesially withdraw a bent archwire from the tube. Additionally, the present invention may also serve to permit free distal crown tipping of a molar tooth which is often desired during treatment without archwire flexing or permanent deformation. More particularly, the buccal tube of the present invention includes a lumen that has a control portion or area at the mesial end to provide control over labiolingual and occlusogingival archwire movement for round and rectangular archwires and also torque control for rectangular archwires, and an occlusal relieved portion distal of the control portion that serves to reduce the force required to mesially withdraw a bent archwire through the tube. Additionally, where the control area is such to define a pivot relationship with a horizontal or level archwire, the relieved portion will also allow distal crown tipping of a molar tooth on which the tube is mounted while preventing mesial crown tipping or flexing of the archwire.

The amount of initial force to draw the bent end of an archwire into the buccal tube of the present invention and the subsequent force thereafter required to pull the archwire the full length of the tube and remove it from the tube may be reduced to a level of about 30 to 40 percent of what would normally be required with a conventional buccal tube. This force reduction translates into enhanced patient comfort. In the area of the lumen that is relieved, the occlusal surface of the lumen is elevated or displaced away from the gingival surface to in effect increase the vertical inside dimension of the lumen. This relieved area may be provided by an inclined surface or a cutout, either of which would serve to reduce the overall force necessary to remove a deformed archwire from the tube. Thus, the occlusal surface is either elevated or lowered depending on whether the tube is for the maxillary (upper) or mandibular (lower) molar. When a rectangular tube is used with a rectangular archwire, this relieved portion does not affect the desired buccal-lingual torque control of the tooth to which the tube is attached, and if the control area enables tipping, the other desired control will not be affected.

Even where the bent end of an archwire is attempted to be straightened in the mouth, it is virtually impossible to completely straighten the wire, and therefore withdrawal of such an archwire from a tube requires the application of some force to the tube on withdrawal. That force, as applied to the tooth, results in discomfort to the patient. The present invention promotes straightening of the remaining bend in the archwire by providing a sloping or relieved surface to the bent wire throughout a substantial part of the lumen and a control area having a shorter length of close-fitting tolerances.

It is therefore an object of the present invention to provide a new and improved buccal tube for archwires that decreases the required force when removing an archwire from the tube where the distal end of the archwire has been bent.

A further object of the present invention is to provide a new and improved buccal tube for archwires that reduces the force needed to withdraw a bent archwire from the tube and permits free distal crown tipping of the tooth on which the tube is mounted, thereby favorably contributing to the results obtainable during treatment.

A further object of the present invention is to provide a buccal tube for archwires that is patient-friendly to reduce the forces required to withdraw a bent archwire from the tube during visits with the orthodontist, thereby reducing patient discomfort.

Other objects, features and advantages of the invention will be apparent from the following detailed disclosure, taken in conjunction with the accompanying sheets of drawings, wherein like reference numerals refer to like parts.

DESCRIPTION OF THE DRAWING

FIG. 1 is a perspective view of a tooth in fragmentary form having the buccal tube of the present invention suitably mounted on the tooth;

FIG. 2 is a side or buccal elevational view of the buccal tube shown in FIG. 1 and mounted on a tooth;

FIG. 3 is a mesial elevational view of the buccal tube of FIG. 1 as mounted on a tooth;

FIG. 4 is a distal elevational view of the buccal tube of FIG. 1 as mounted on a tooth;

FIG. 5 is a longitudinal sectional view taken through the buccal tube of FIG. 1 and illustrating the withdrawal of an archwire having a bent distal end;

FIG. 6 is a vertical cross-sectional view taken substantially along line 6—6 of FIG. 5;

FIG. 7 is a vertical cross-sectional view taken substantially along line 7—7 of FIG. 5;

FIG. 8 is a longitudinal sectional view taken through a modified molar tube of the invention;

FIG. 9 is a longitudinal sectional view of a still further modified molar tube of the present invention;

FIG. 10 is a distal elevational view of the buccal tube of FIG. 9 and showing the position of the distal end of the archwire;

FIG. 11 is a mesial elevational view of the buccal tube of FIG. 9;

FIG. 12 is a view similar to FIG. 8 of a further modification wherein the pivot allowing the tipping of the tube is mesially offset and further illustrating the tube in tipped position; and FIG. 13 is a longitudinal sectional view taken through a buccal tube of the prior art to illustrate the advantages of the present invention.

DESCRIPTION OF THE INVENTION

Referring to the drawings, and particularly to FIGS. 1 to 7, the buccal tube of the present invention, generally designated as 15, is shown as being attached to a band 16 mounted on a molar tooth 17 for the purpose of anchoring the distal end of an archwire 18. The long axis of the tube or the mesial-distally extending axis is substantially perpendicular to the long axis of the tooth on which it is mounted. It will be appreciated that the band 16 may be of any suitable type that is preferably made of stainless steel and suitably cemented to the molar tooth 17. However, the buccal tube may also be mounted on a bondable base for bonding directly to a tooth. It should also be appreciated that it is preferable to construct the buccal tube of stainless steel although any other suitable materials may be used.

The molar tube illustrated in FIGS. 1 to 7 includes a rectangular in cross section elongated body 20 having a lumen 22 extending therethrough that is sized to receive the rectangular archwire 18. It will be appreciated that the shape of the body 20 may be other than as illustrated and also that the buccal tube may be a part of an appliance having other elements such as a tube for receiving headgear or a lip bumper and which also may include a suitable hook for connecting elastics to other appliances along the arch. The tube illustrated is for an upper right molar and would likewise be usable on a lower right molar by being axially rotated 180 degrees about its longitudinal or mesial-distal axis. Further, it should be appreciated that, as with all such tooth-mounted appliances, the exterior edges would be rounded to enhance their comfort in the mouth. When a tube is made by casting, the interior edges normally include a radius of about 0.005 inch (0.125 mm), but such a radius is not adequate to provide any suitable reduction of the withdrawal forces needed.

As previously mentioned, the buccal tube of the invention serves to anchor distal ends of an archwire wherein the archwire would be received within the lumen and, depending upon the amount of archwire material protruding from the distal end of the tube, usually trimmed and bent as shown in FIGS. 1, 2, and 5. Preferably, the distal end of the wire is bent gingivally as illustrated. This bend in the wire then serves to prevent the archwire from moving mesially through the tube during treatment which, if permitted, could lead to opening of spaces between teeth along the arch.

Subsequent to the cutting and/or bending of the distal end of the archwire, it is often necessary to withdraw the wire from the tube. This necessity may occur during any or all of the visits that a patient would periodically make with an orthodontist. It is principally at this time that the buccal tube of the present invention becomes advantageous inasmuch as the force required to mesially withdraw the archwire is substantially reduced by the present invention. This reduction is obtained by the unique formation of the lumen 22, as shown in FIG. 2.

The lumen 22 includes a control portion or area 25 and a relieved portion or area 26. Depending on the mesial-distal length of the occlusal wall or side of the control area, the control area may or may not allow pivotal movement between the archwire and the tube, as explained below. It will be appreciated that the buccal tube 15 includes four outside walls: a gingival wall 29, an occlusal wall 30, a buccal wall 31, and a lingual wall 32. Similarly, the lumen includes a gingival wall or side 35, an occlusal wall or side 36, a buccal wall or side 37, and a lingual wall 38. In the illustrated embodiment of FIGS. 1 to 7, the gingival wall 35 extends substantially parallel to the outer gingival wall 29 and throughout the entire length of the tube and the control and relieved areas. Similarly, the buccal and lingual walls 37 and 38 of the lumen are essentially parallel to the outside buccal and lingual walls 31 and 32 respectively throughout both the control and relieved areas. However, the occlusal wall 36 of the lumen is inclined to the outside occlusal wall 30 in the area of the relieved portion and essentially parallel to the outside occlusal wall 30 in the area of the control portion where the control area includes a width that will not allow tipping. Thus, the occlusal wall 36 of the lumen is somewhat lowered at the distal end 40 although it would be the opposite and elevated for a buccal tube on the lower arch. Further, the control area 25 at the mesial end 41 of the tube would be sized to closely receive the archwire so that in the control zone or area the buccal tube would provide the desired control at least along a transverse plane of the archwire. Preferably, the clearance along all sides of the archwire with respect to the lumen at the control zone would be about ±0.001 inch (0.025 mm).

As previously explained, the mesial-distal length and/or position of the occlusal side of the control area will determine whether pivotal movement may be possible between the archwire and the tube to allow distal crown tipping. Further, the occlusal side may be formed to enhance tipping. If the mesial-distal length of the occlusal side is such as to define a flat wall to the archwire and is opposite a similar flat gingival wall, no pivotal movement can exist and no tipping will be possible. However, if the mesial-distal length of the occlusal side is small or mesial to the opposing gingival wall (side) as seen in FIG. 12 such that the occlusal side of the control area allows a pivotal relation to be established with the archwire, distal crown tipping of the molar may be possible.

Even though the bent end 18a of the archwire would be straightened as much as possible before removal, a bend to some degree would still remain in the wire, as illustrated in FIG. 5. The sloping occlusal surface 36 would coact with the gingival surface or wall 35 to effect a straightening action on the bent end of the archwire as it moves mesially through the tube, wherein the lower corner of the bend would basically bear against the occlusal wall 36, while the upper corner of the distal end of the wire would bear against the gingival wall 35. The amount of force required to withdraw the wire would be substantially less than that required to withdraw the wire from heretofore known buccal tubes as illustrated in FIG. 13, thereby enhancing the comfort of the patient during this procedure. Not only would the maximum amount of force be reduced as needed to withdraw the wire but also the work required (force×distance) would still be reduced because the temporarily deformed bent end of the wire could be moved through the length of the lumen with less force. On the other hand, with respect to the prior art and as shown in FIG. 13, the pulling of the archwire for removal requires the highest level of force to move the bent portion the full length of the lumen.

Thus, the lumen configuration in the buccal tube of the invention promotes straightening of the remaining bend in the archwire and provides an elongated enlarged relieved area 26 through which the bent end of the archwire can be pulled with less force until the wire must further temporarily deform at the control zone of the lumen where the minimum inside dimensions are briefly encountered. The enlarged area of the lumen preferably extends between about 80 and 95 percent of the length of the lumen, while the control area extends between about 5 and 20 percent of the length of the lumen, all of which depend on whether tipping is to be permitted as above mentioned. Depending on tolerances, a control area of about 1 to 5 percent would allow tipping. Also, where tipping would be desired, the pivot could be offset mesially of the main body of the tube.

During treatment and when the archwire is received within the lumen of the buccal tube, the gingival surface of the archwire will mate with the gingival wall 35 of the lumen. Likewise, the opposite sides of the archwire 18 will mate with the opposed side walls of the lumen. Except for in the control area or zone of the lumen, the occlusal side of the archwire will be variably spaced from the occlusal wall of the lumen. During normal operation, the plane of the archwire received by the tube-will be parallel to the tube, and also parallel to the occlusal plane and the archwire on the opposing arch. By providing an inclined occlusal lumen wall and a parallel gingival wall, the tooth is prevented against mesial crown tipping but would be allowed distal crown tipping, although limited by the occlusal wall. Thus, a second feature of the buccal tube of the invention is that it would permit the desired controlled distal crown tipping.

With respect to the above described ability of the buccal tube of the invention to permit molar crowns to tip distally, there are occasions when it is desirable to tip maxillary molar crowns distally to create better relationships with opposing teeth and/or to retract all of the teeth in the arch. The particular lumen in the tube of the present invention allows distal crown tipping of the tube/tooth in the presence of a straight archwire. This distal tipping would not in turn deflect the anterior of the archwire incisally which if permitted would cause a deepening of the bite as is the case with all existing molar tubes.

Another embodiment of the invention is shown in FIG. 8 wherein a modified buccal tube 15A differs from the buccal tube 15 in that the relieved area of the lumen is defined by lowering the occlusal wall 36a substantially equally in the entire relieved area 26a and only defining a sloped surface 36b adjacent the mesial end of the tube. This embodiment illustrates that the form of the relieved portion may take other shapes and still produce substantially the same results. Generally speaking, mesial withdrawal of an archwire from the tube 15A will achieve the same results as removal of the archwire from the lumen in the buccal tube 15. However, it can be appreciated that the bent area may not have any resistance to being withdrawn until it reaches the sloped portion 36b just distal of the control zone 25a. At that point, the sloped wall will assist in straightening the bent end of the wire as it is withdrawn through the control zone or area 25a. This embodiment also has the occlusal side of the control area formed to define a pivot relation with the archwire when distal tipping occurs. The occlusal side is in the form of a rounded edge that contacts the occlusal side of the archwire.

A further embodiment of the invention is shown in FIG. 12, which differs from the embodiment of FIG. 8 only in that the pivot for the buccal tube is offset at the mesial end of the tube and disposed mesial of the gingival side of the lumen. The control portion constitutes the pivot and the mesial end of the gingival side of the lumen. This embodiment is generally designated as 15B, and it will be appreciated that limited free distal crown tipping relative to the level archwire may be provided similar to the embodiment of FIG. 8.

It should likewise be appreciated that the buccal tube of the present invention may be used for archwires having any suitable cross section and the further embodiment 15C shown in FIGS. 9 to 11 illustrates a round archwire 45 received in a lumen 44 having a round cross section at the control zone 46 and a somewhat elliptical cross section at the relieved portion 47. Withdrawal of the round wire with the bent end 45a will function similarly to withdrawal of the rectangular wire from the buccal tube 15 as the bent end will tend to straighten as it is withdrawn through the relieved portion and ultimately through the control portion. It will be appreciated that the control portion 46 affects complete circumferential-labiolingual and occlusogingival control around the round archwire 45 except that the tube can rotate relative to the archwire unlike the action of a rectangular lumen with respect to a rectangular wire. Even though the occlusal side is sloping, the relieved portion 47 prevents labial-lingual and occlusal movement between the archwire and the tube/tooth. Further, it will be appreciated that the buccal tube 15C will also serve to prevent mesial crown tipping while allowing distal crown tipping in the presence of a straight, horizontal archwire in substantially the same fashion as above explained with respect to the previous embodiments.

From the foregoing, it will be appreciated that the buccal tube of the present invention increases the well-being of the patient by reducing the discomfort associated with the withdrawal of an archwire from a buccal tube. Both the magnitude and the duration of the removal force is reduced. Further, the buccal tube of the present invention includes a lumen that not only reduces archwire withdrawal forces but can also permit distal crown tipping of the molar on which the tube is mounted.

It will be understood that modifications and variations may be effected without departing from the scope of the novel concepts of the present invention, but it is understood that this application is to be limited only by the scope of the appended claims.

The invention is hereby claimed as follows:

1. A buccal tube adapted to be secured to a tooth comprising:

a lumen extending mesial-distally therethrough for receiving the distal end of an archwire, said lumen having a mesial end and a distal end, said lumen including a control portion at said mesial end for closely receiving the archwire to exert labiolingual and occlusogingival control over the archwire, and a substantially occlusal gingival relieved portion extending from the control portion to the distal end to reduce the force required for the mesial withdrawal of an archwire having a bend distal to the tube.

2. The buccal tube of claim 1, wherein the control portion of the lumen is rectangular in cross section for receiving a rectangular archwire, and the control portion further provides torque control.

3. The buccal tube of claim 1, wherein the control portion of the lumen is round in cross section for receiving a round archwire.

4. The buccal tube of claim 1, wherein the mesial-distal length of the occlusal side of the control portion is such as to prevent the tube from tipping relative to the archwire.

5. The buccal tube of claim 1, wherein the lumen includes a gingival wall adapted to be in engagement with the gingival surface of a level archwire to prevent mesial crown tipping of the tooth, and the occlusal side of the control portion defines a pivot to permit distal crown tipping of the tooth.

6. In a buccal tube adapted to be mounted on a tooth and having a lumen extending therethrough for receiving the distal end of a horizontal archwire, the archwire extending through the lumen and being bent at the distal end to prevent retraction through the lumen, said lumen including a control area at the mesial end mating closely with the archwire, and a substantially occlusal-gingival relieved area opening to the distal end for reducing the amount of force required to withdraw the archwire from the tube.

7. The buccal tube of claim 6, wherein the control area of the lumen includes a rectangular cross section for use with a rectangular archwire.

8. The buccal tube of claim 6, wherein the control area of the lumen includes a circular cross section for use with a round archwire.

9. The buccal tube of claim 8, wherein the relieved area includes gingival, lingual, and buccal sides mating with the respective sides of the archwire, and an occlusal side spaced from the occlusal side of the archwire.

10. The buccal tube of claim 9, wherein the occlusal side of the relieved area is inclined occlusally from the control area to the distal end of the relieved area.

11. The buccal tube of claim 9, wherein the occlusal side of the relieved area generally parallels the gingival side thereof.

12. The buccal tube of claim 10, wherein the occlusal side of the control area is formed to prevent tipping of the tooth.

13. The buccal tube of claim 10, wherein the occlusal side of the control area is formed to allow tipping of the tooth.

14. The buccal tube, of claim 13, wherein the occlusal side limits distal crown tipping of the tooth.

15. A buccal tube for receiving and anchoring the distal end of a horizontal archwire to a molar tooth which comprises:

a tubular body having an archwire receiving lumen extending mesial-distally therethrough, said lumen including a control portion at the mesial end for matingly receiving the archwire, and a substantially occlusal-gingival relieved portion extending from the control portion to the distal end of the lumen to reduce the force required for the mesial withdrawal of an archwire having a bend therein distal to the tube.

16. The buccal tube of claim 15, wherein the relieved portion is configured to allow limited distal crown tipping of the tube/tooth.

17. The buccal tube of claim 15, wherein the control portion of the lumen is rectangular in cross section for receiving a rectangular archwire.

18. The buccal tube of claim 15, wherein the control portion of the lumen is round in cross section for receiving a round archwire.

* * * * *